United States Patent [19]

Taniguchi et al.

[11] Patent Number: 4,533,712

[45] Date of Patent: Aug. 6, 1985

[54] PROCESS FOR THE PRODUCTION OF HIGH MOLECULAR WEIGHT ORGANOALUMINUM POLYMERS

[75] Inventors: Isoji Taniguchi, Kyoto; Yoshiharu Kimura, Ohmihachiman; Toshiaki Ichimura, Toyonaka, all of Japan

[73] Assignee: Idemitsu Kosan Company Limited, Tokyo, Japan

[21] Appl. No.: 586,075

[22] Filed: Mar. 5, 1984

[30] Foreign Application Priority Data

Mar. 30, 1983 [JP] Japan .................................. 58-56266
May 7, 1983 [JP] Japan .................................. 58-79837

[51] Int. Cl.$^3$ ...................... C08G 67/00; C08G 63/66; C08G 63/68
[52] U.S. Cl. ........................................ 528/9; 528/271; 528/395
[58] Field of Search ............................. 528/9, 271, 395

[56] References Cited

U.S. PATENT DOCUMENTS 2,744,074 5/1956 Theobald .............................. 528/9
2,844,551 7/1958 Orthner et al. ...................... 528/395
4,069,236 1/1978 Hutchison et al. .................. 528/395

FOREIGN PATENT DOCUMENTS 541843 6/1957 Canada ................................. 528/395
783679 9/1957 United Kingdom ................. 528/395

*Primary Examiner*—Wilbert J. Briggs, Sr.
*Attorney, Agent, or Firm*—Frishauf, Holtz, Goodman & Woodward

[57] ABSTRACT

A process for producing a high molecular weight organoaluminum polymer by using an organoaluminum compound containing an acyloxy group, water and an organic acid.

The organoaluminum polymer obtained herein is suitable for preparing fibers.

10 Claims, No Drawings

PROCESS FOR THE PRODUCTION OF HIGH MOLECULAR WEIGHT ORGANOALUMINUM POLYMERS

BACKGROUND OF THE INVENTION

Materials of high strength and super heat resistance have recently been desired in various industrial fields. Among such materials are alumina fibers which are suitable for use in fabrication of composite materials in combination with metals, ceramics and so forth.

A method of calcining fiber precursors made of organoaluminum polymers has received increasing attention for the production of superior alumina fibers. However, a method has not been developed yet which produces with ease and further with high efficiency high molecular weight organoaluminum polymers which are suitable for use in production of such fiber precursors. That is although it is known that organoaluminum polymers can be prepared by reacting organoaluminum compounds with water, high molecular weight organoaluminum polymers suitable for use in preparing, e.g., fibers are difficult to produce by conventional procedures.

SUMMARY OF THE INVENTION

An object of the present invention is to provide a process for efficiently producing high molecular, weight organoaluminum polymers suitable for use in preparing, e.g., fibers.

The present invention relates to a process for producing a high molecular weight organoaluminum polymer by reacting an organoaluminum compound with water, which process is characterized in that as reactants an organoaluminum compound represented by the general formula:

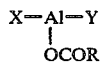

(wherein X and Y may be the same or different and are each a hydrogen atom, an alkyl group, or an alkoxyl group, and R is at least one organic radical) is used and an organic acid is used in an amount of from 0.2 to 10 moles per mole of the organoaluminum compound.

DETAILED DESCRIPTION OF THE INVENTION

The organoaluminum compounds as used herein, as described above, have the following general formula (I):

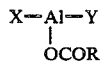

(wherein X and Y may be the same or different and are each a hydrogen atom, an alkyl group or an alkoxyl group, and R is at least one organic radical).

The alkyl group represented by X and Y includes a methyl group, an ethyl group, a n-propyl group, an iso-propyl group, a n-butyl group and its isomers (e.g., an isobutyl group, a sec-butyl group, and a tert-butyl group), a n-pentyl group and its isomers, and a n-hexyl group and its isomers.

The alkoxyl group includes a methoxyl group, an ethoxyl group, a n-propoxyl group, an iso-propoxyl group, a n-butoxyl group and its isomers, a n-pentoxyl group and its isomers, and a n-hexanoxyl group and its isomers.

In the general formula (I), R represents at least one organic radical. The organic radical includes a saturated or unsaturated aliphatic substituent, an alicyclic substituent, and an aromatic substituent.

Specifically the saturated aliphatic substituent includes a methyl group, an ethyl group, a n-propyl group, an isopropyl group, a n-butyl group and its isomers, a n-pentyl group and its isomers, and a n-nonyl group and its isomers.

The alicyclic substituent includes a cyclohexyl group.

The unsaturated aliphatic substituent includes an alkenyl group (e.g., a vinyl group, an allyl group, and a crotyl group), an unsaturated, mono-, di-, tri- or like, hydrocarbon group (e.g., a butadienyl group and an octatrienyl group), and an alkinyl group (e.g., an-ethinyl group and a propinyl group).

The aromatic substituent includes various aryl groups such as a phenyl group, a tolyl group, an anisyl group, and a naphthyl group.

The saturated aliphatic substituent, unsaturated aliphatic substituent, alicyclic substituent, and aromatic substituent may contain at least one radical, such as a chlorine atom, an amino group, a hydroxyl group, a carboxyl group, an alkoxyl group, and an aryl group.

In the process of the present invention, a mixture of two or more organoaluminum compounds in which R represents different organic radicals can be used.

In accordance with the process of the present invention, organic acids are added in the reaction of the organoaluminum compounds represented by the formula (I) and water. Most of the known organic acids can be used in the present invention. Suitable examples are saturated or unsaturated aliphatic monocarboxylic acids (excluding formic acid), alicyclic carboxylic acids, aromatic monocarboxylic acids, dicarboxylic acids, hydroxycarboxylic acids, and their derivatives containing a substituent or substituents in the main chain thereof.

Typical examples of the saturated aliphatic monocarboxylic acids are acetic acid, propionic acid, butyric acid, isobutyric acid, pivalic acid, octanoic acid, lauric acid, and stearic acid.

Typical examples of the unsaturated aliphatic monocarboxylic acids are acrylic acid, methacrylic acid, crotonic acid, and oleic acid.

A typical example of the alicyclic carboxylic acids is cyclohexanecarboxylic acid.

Typical examples of the aromatic monocarboxylic acids are succinic acid, glutaric acid, phthalic acid, and cyclohexanedicarboxylic acids.

Typical examples of the hydroxycarboxylic acids are glycolic acid, lactic acid, and mandelic acid.

Typical examples of the substituents of the above-described carboxylic acid derivatives are a chlorine atom, an amino group, a hydroxyl group, a carboxyl group, an alkoxyl group, a phenyl group, and an aryl group.

As the organic acid to be added in the reaction of the organoaluminum compound and water, it is preferred that organic acids identical to those (RCOOH) corresponding to the organic radicals (R) of the organoaluminum compound used herein or organic acids higher in acidity than those (RCOOH) be used.

For example, when the organic radical of the organoaluminum compound to be used in the reaction is an undecyl group, since the corresponding organic acid is lauric acid, it is preferred that lauric acid or organic acids having an acidity higher than that of lauric acid be used as the organic acids.

Typical examples of these organic acids include hexanoic acid, butyric acid, valeric acid, acetic acid, methacrylic acid, and acrylic acid. Although typical organic acids of the saturated or unsaturated aliphatic monocarboxylic acids are listed above, the present invention is not limited thereto.

In the present invention, the above-described organic acids may be used singly or in combination with each other.

In the practice of the present invention, the organoaluminum compound, water, and organic acid may be used as such or without use of any solvents. In general, however, it is preferred for them to be diluted with suitable organic solvents for convenience of handling and also for effective condensation polymerization. In particular, when solid acids are used as the organic acids, they are preferably used after dilution with organic solvents.

Any organic solvents can be used as long as they are capable of dissolving the organoaluminum compounds, water, and organic acids and, furthermore, do not react therewith. Typical examples are hydrocarbon solvents such as benzene, toluene, xylene, tetralin, decalin, pentane, hexane, and heptane; ether solvents such as dioxane, diethyl ether, 1,2-dimethoxyethane, tetrahydrofuran, and anisol; tert-amine solvents such as pyridine, picoline, and triethylamine; and polar solvents such as dimethylsulfoxide and dimethylformamide.

In the condensation polymerization of the organoaluminum compound and water, water may be added at once but it is preferred to gradually add dropwise. It is also convenient for handling that water is used in the form of solutions with suitable organic solvents. In the case of the organic acids, they may be added at once but it is preferred for them to gradually add dropwise as in the case of water.

The order in which the organoaluminum compound, water, and organic acid are added is not critical in the process of the present invention, but it is convenient to determine the order in which water and the organic acid are added to the organoaluminum compound.

With regard to the order of addition of the organic acid, it may be added in the course of the condensation polymerization between the organoaluminum compound and water, or after the condensation polymerization, or water may be added after the organic acid is added to the organoaluminum compound.

Furthermore, the following procedures (i), (ii) may be employed; (i) part of the organic acid is added in the course of the condensation polymerization between the organoaluminum compound and water, and then the remaining organic acid is added after completion of the condensation polymerization, (ii) the organic acid is added to the polymer formed by the condensation polymerization.

The organic acid is added in an amount of from 0.2 to 10 moles, preferably from 0.5 to 3.5 moles, per mole of the organoaluminum compound. If the organic acid is added within the range as defined above, there can be formed organoaluminum polymers which have an increased molecular weight and thus are suitable for use in production of fibers. If the amount of the organic acid added is less than 0.2 mole per mole of the organoaluminum compound, there can be obtained almost no increase in the molecular weight of the organoaluminum polymers. On the other hand, if the amount of the organic acid added is in excess of 10 moles per mole of the organoaluminum compound, the molecular weight of the organoaluminum polymers is scarcely increased.

The amount of water to be used in the condensation polymerization of the organoaluminum compound is not critical and can be determined appropriately. Usually it is effective for the production of high molecular weight organoaluminum polymers that water be used in an amount of from 1.0 to 3.5 moles per mole of the organoaluminum compound. Especially preferred is the range of from 1.0 to 2.0 moles per mole of the organoaluminum compound. If the amount of water added is too small, there cannot be formed high molecular weight organoaluminum polymers. On the other hand, if the amount of water added is too large, the condensation polymerization reaction is accelerated, resulting in the formation of organoaluminum polymers which are excessively polymerized, and cross-linked and thus are insoluble in water. However, when at least one of X and Y in the formula (I) represents an alkoxyl group, water can be added in an amount of less than 1.0 mole per mole of the organoaluminum compound, since water is formed in the condensation polymerization reaction.

The reaction temperature in the process of the present invention is not critical as long as it is not more than 200° C. Preferably the reaction temperature is chosen depending on the type of the organoaluminum compound, organic acid, or organic solvent. In commercial practice of the present invention, it is economical for the condensation polymerization reaction to be performed at a temperature ranging between about 0° and 60° C.

The organoaluminum polymers produced by the process of the present invention have a reduced viscosity of from 0.4 to 5.5 (solvent: a mixed solvent of equal weights of tetrachloroethane and phenol; temperature: 30° C.; concentration: 0.5 grams per deciliter); that is, they are high molecular weight polymers suitable for spinning and so forth.

On the other hand, in accordance with conventional methods even if the amount of water added is from 1.0 to 1.2 moles per mole of trialkyl aluminum such as triethyl aluminum, there can be formed only low molecular weight organoaluminum polymers having a reduced viscosity of 0.2 or less.

The present invention is described in greater detail with reference to the following examples, although the present invention is not limited thereto.

EXAMPLE 1

A mixture of 15 grams (58 millimoles) of diisobutylaluminum 3-ethoxypropionate prepared from triisobutylaluminum and ethoxypropionic acid, and 30 milliliters of tetrahydrofuran was placed in a three-necked flask equipped with a dropping funnel, a reflux condenser, and a three-way cock, and 10 milliliters of a tetrahydrofuran solution containing 1.04 grams (58 millimoles) of distilled water and 3.44 grams (29 millimoles) of ethoxypropionic acid were gradually added dropwise thereto and reacted at room temperature in a nitrogen atmosphere while stirring with a magnetic stirrer. On allowing the reaction mixture to stand overnight at room temperature, there was formed a uniform, clear and viscous solution. This solution showed a good stringiness at room temperature, said stringiness being a measure of fiber molding.

The solution was then poured into 500 milliliters of hexane and reprecipitated to yield 11.6 grams of a white organoaluminum polymer in a powder form. The reduced viscosity of the polymer as determined in a mixed solvent of equal weights of phenol and tetrahydrofuran (concentration: 0.5 gram per deciliter; temperature: 30° C.) was 1.01.

EXAMPLE 2

In the same atmosphere and apparatus as used in Example 1, 1.26 grams (70 millimoles) of water and 2.4 grams (12 millimoles) of lauric acid were added to a mixture of 16.5 grams (58 millimoles) of diethylaluminum laurate, which had been prepared by reacting triethylaluminum and lauric acid, and 30 milliliters of tetrahydrofuran, and reacted at 60° C. In several hours, the reaction mixture became a uniform, viscous solution. The tetrahydrofuran was distilled off under reduced pressure, and the residue was washed with hexane and dried, yielding 14 grams of a white organoaluminum polymer in a resin form.

The reduced viscosity of the polymer in tetrahydrofuran (concentration: 0.5 gram per deciliter; temperature: 30° C.) was 2.41.

EXAMPLE 3

The procedure of Example 2 was repeated wherein 6.03 grams (58 millimoles) of 3-methoxypropionic acid was used as the organic acid in place of lauric acid. On allowing the reaction mixture at 0° C. for one day and night, a uniform, viscous solution was obtained as in Example 2. The solution was poured into a large amount of hexane to yield 13.5 grams of a white organoaluminum polymer in a powder form.

The reduced viscosity of the polymer in a mixed solvent of equal weights of phenol and tetrahydrofuran (concentration: 0.5 gram per deciliter; temperature: 30° C.) was 1.6.

EXAMPLE 4

In the same atmosphere and apparatus as used in Example 1, 0.45 gram (25 millimoles) of water and 9.0 grams (125 millimoles) of propionic acid were added simultaneously to 5.8 grams (25 millimoles) of isopropoxy sec-butoxyaluminum propionate and 50 milliliters of a benzene solution and reacted at room temperature.

The reaction mixture was allowed to stand overnight and then poured into hexane and reprecipitated to yield 3.81 grams of a polymer. The reduced viscosity of the polymer in a mixed solvent of equal weights of phenol and tetrahydrofuran (concentration: 0.5 gram per deciliter; temperature: 30° C.) was 0.77.

EXAMPLE 5

In the same atmosphere and apparatus as used in Example 1, 0.68 gram (38 millimoles) of water and 3.05 grams (25 millimoles) of benzoic acid were added to 20 milliliters of a decalin solution containing a mixture of diisopropoxyaluminum benzoate and isopropoxy sec-butoxyaluminum benzoate which had been prepared by reacting 5.45 grams (25 millimoles) of diisopropoxyaluminum sec-butoxide and 3.05 grams (25 millimoles) of benzoic acid, and reacted at 50° C. The reaction mixture was allowed to stand overnight at 50° C. Thereafter, the same procedure as in Example 4 was repeated to yield 5.3 grams of an organoaluminum polymer. The reduced viscosity of the polymer in dimethylformamide (concentration: 0.5 gram per deciliter; temperature: 30° C.) was 3.1.

EXAMPLE 6

A mixture of 11.7 grams (58 millimoles) of diethylaluminum 3-ethoxypropionate prepared from triethyl aluminum and 3-ethoxypropionic acid and 40 milliliters of tetrahydrofuran was placed in a three-necked flask equipped with a dropping funnel, a reflux condenser, and a three-way cock, and 10 milliliters of a tetrahydrofuran solution containing 1.37 grams (12 millimoles) of 3-ethoxypropionic acid was gradually added dropwise and reacted at room temperature in a nitrogen atmosphere. Then, 10 milliliters of a tetrahydrofuran solution containing 1.04 grams (58 millimoles) of distilled water was gradually added dropwise. The reaction mixture gradually became a viscous solution. The solution was allowed to stand at room temperature for one day and night, and then poured into 500 milliliters of hexane and reprecipitated to yield 10.8 grams of a white organoaluminum polymer in a powder form.

The reduced viscosity of the polymer in a mixed solvent of equal weights of phenol and tetrachloroethane (concentration: 0.4 gram per deciliter; temperature: 30° C.) was 0.40.

EXAMPLE 7

In the same atmosphere and apparatus as used in Example 6, 23.2 grams (116 millimoles) of lauric acid was added to 80 milliliters of a toluene solution containing 20 grams (58 millimoles) of diisopropoxyaluminum laurate and reacted at 60° C. for 2 hours. Then, 10 milliliters of a dioxane solution containing 1.26 grams (70 millimoles) of distilled water was added dropwise at the same temperature as above and reacted for additional 8 hours.

The reaction mixture was cooled, and then poured into a large amount of pentane and reprecipitated to yield 21 grams of a white organoaluminum polymer in a powder form.

The reduced viscosity of the polymer in tetrahydrofuran (concentration: 0.5 gram per deciliter; temperature: 30° C.) was 1.8.

EXAMPLE 8

In the same atmosphere and apparatus as used in Example 6, 10 milliliters of a tetrahydrofuran solution containing 1.04 grams (58 millimoles) of distilled water was gradually added dropwise at room temperature to 30 milliliters of a tetrahydrofuran solution containing 9.16 grams (58 millimoles) of diethylaluminum propionate prepared from triethylaluminum and propionic acid. After the addition was completed, the mixture was stirred for several hours at the same temperature as above. Subsequently, 4.3 grams (58 millimoles) of propionic acid was added to the reaction mixture and was allowed to stand overnight at room temperature. The mixture became a viscous solution, and it was then reprecipitated in a large amount of hexane to yield 8.9 grams of a white organoaluminum polymer in a powder form.

The reduced viscosity of the polymer in a mixed solvent of equal weights of phenol and tetrachloroethane (concentration: 0.4 gram per deciliter; temperature: 30° C.) was 5.05.

EXAMPLE 9

In the same atmosphere and apparatus as used in Example 6, 10 milliliters of a tetrahydrofuran solution containing 0.45 gram (25 millimoles) of distilled water was gradually added dropwise at −78° C. to a solution of 8.5 grams (25 millimoles) of diisobutylaluminum laurate in 20 milliliters of tetrahydrofuran, said diisobutylaluminum laurate being prepared from triisobutyl aluminum and lauric acid. After the addition was completed, the mixture was raised in temperature to room temperature and stirred at room temperature for additional 1 hour. Subsequently, 2.6 grams (25 millimoles) of 3-methoxypropionic acid was added, and the resulting mixture was allowed to stand at room temperature for 12 hours. The mixture became a viscous solution. This solution was reprecipitated in a large amount of hexane to yield 4.2 grams of a white organoaluminum polymer in a powder form.

The reduced viscosity of the polymer in a mixed solvent of equal weights of phenol and tetrachloroethane (concentration: 0.4 gram per deciliter; temperature: 30° C.) was 0.97.

EXAMPLE 10

In the same atmosphere and apparatus as used in Example 6, 0.45 gram (25 millimoles) of water was added to 50 milliliters of a benzene solution containing 5.8 grams (25 millimoles) of isopropoxy sec-butoxyaluminum propionate and reacted at room temperature for 1 hour. Subsequently, 9.0 grams (125 millimoles) of propionic acid was added and stirred at room temperature for 5 hours. Then the resulting mixture was poured into hexane and reprecipitated to yield 3.8 grams of a white polymer in a powder form.

The reduced viscosity of the polymer in a mixed solvent of equal weights of phenol and tetrachloroethane (concentration: 0.5 gram per deciliter; temperature: 30° C.) was 0.83.

EXAMPLE 11

In the same atmosphere and apparatus as used in Example 6, a mixed solvent of 58 millimoles of water and 20 milliliters of dioxane was added dropwise at 0° C. to 11.7 grams (58 millimoles) of diethylaluminum 3-ethoxypropionate prepared from triethylaluminum and 3-ethoxypropionic acid, and reacted with each other.

Then, the reaction mixture was allowed to stand at room temperature for one day and night, and then poured into a large amount of hexane and reprecipitated to yield 9.2 grams of a product. This product was oligomer of poly(acyloxyaloxane) represented by

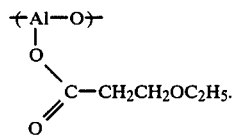

One gram ($6.2 \times 10^{-3}$ unit mole) of the oligomer was added into 10 milliliters of tetrahydrofuran, and was reacted with a prescribed amount of 3-ethoxypropionic acid at room temperature for 10 hours to obtain polymer product.

The polymer products was poured into a large amount of hexane and isolated by reprecipitation. The reduced viscosity of the polymer products were determined. The results obtained are shown in Table 1.

TABLE 1

| Run | [EPA]/[A1 unit]*[1] | ηsp/c*[2] |
|-----|---------------------|-----------|
| 1 | 0.4 | 0.33 |
| 2 | 0.7 | 0.95 |
| 3 | 1.1 | 0.47 |

*[1] Molar ratio of 3-ethoxypropionic acid (EPA) to aluminum unit in the oligomer.
*[2] Reduced viscosity determined in a mixed solvent of equal weight of phenol and tetrachlorofuran (concentration: 0.4 gram per deciliter; temperature: 30° C.).

What is claimed is:

1. A process for producing a high molecular weight organoaluminum polymer by reacting an organoaluminum compound with water, the improvement comprising using as reactants an organoaluminum compound represented by the general formula:

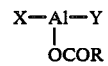

(wherein X and Y may be the same or different and are each a hydrogen atom, an alkyl group, or an alkoxyl group, and R is at least one organic radical) and an organic acid in an amount of from 0.2 to 10 moles per mole of the organoaluminum compound.

2. The process as claimed in claim 1, wherein the molar ratio of the water to the organoaluminum compound is from 1:1 to 3.5:1.

3. The process as claimed in claim 1, wherein the organic acid is added during the reaction of the organoaluminum compound and water.

4. The process as claimed in claim 1, wherein the organic acid is added prior to the reaction of the organoaluminum compound and water.

5. The process as claimed in claim 1, wherein the organic acid is added after the reaction of the organoaluminum compound and water.

6. The process as claimed in claim 1, wherein a part of the organic acid is added during the reaction of the organoaluminum compound and water, and the remainder is added after completion of the reaction.

7. The process as claimed in claim 2, wherein the organic acid is added during the reaction of the organoaluminum compound and water.

8. The process as claimed in claim 2, wherein the organic acid is added prior to the reaction of the organoaluminum compound and water.

9. The process as claimed in claim 2, wherein the organic acid is added after the reaction of the organoaluminum compound and water.

10. The process as claimed in claim 2, wherein a part of the organic acid is added during the reaction of the organoaluminum compound and water, and the remainder is added after completion of the reaction.

* * * * *